US00PP12557P2

(12) United States Plant Patent
Olesen et al.

(10) Patent No.: US PP12,557 P2
(45) Date of Patent: Apr. 23, 2002

(54) ROSE PLANT NAMED 'POULDRIK'

(76) Inventors: L. Pernille Olesen; Mogens Olesen, both of Hillerodvejen 49, Fredensborg (DK), DK-3480

( * ) Notice: Subject to any disclaimer, the term of this patent is extended or adjusted under 35 U.S.C. 154(b) by 0 days.

(21) Appl. No.: 09/276,894

(22) Filed: Mar. 25, 1999

(51) Int. Cl.[7] ..... A01H 5/00
(52) U.S. Cl. ..... Plt./149
(58) Field of Search ..... Plt./149, 148, 141, Plt./147

(56) References Cited

U.S. PATENT DOCUMENTS

PP381 P * 4/1940 De Ruiter ..... 47/61
PP1,897 P * 1/1960 Swim ..... 47/61

OTHER PUBLICATIONS

UPOV–ROM GTITIM Computer Database 2000/06, Dec. 8, 2000, GTI Jouve Retrieval Software, citation for 'Pouldrik'.*

Poulsen Roser Pacific "Plant Breeders' Rights Application Form" Mar. 3, 1998 5 pages Canada.

Research Center for Cultivar Testing "Decision" Feb. 14, 1997 1 page Poland.

Community Plant Variety Office "Certificate on the Grant of Community Plant Variety Rights" Jul. 6, 1998 7 pages European Union.

Community Plant Variety Office "Receipt" Aug. 28, 1995 4 pages European Union.

Community Plant Variety Office "Chapter 1: Applications" Feb. 26, 1996 2 pages EU.

Community Plant Variety Office "Chapter 4:Decisions" Oct. 15, 1998. 2 pages EU.

* cited by examiner

*Primary Examiner*—Bruce R. Campell
*Assistant Examiner*—June Hwu

(57) ABSTRACT

A new garden rose plant which has abundant, coral pink flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between MACrexy (U.S. Plant Pat. No. 6,713) and an unnamed seedling (non-patented). The two parents were crossed and the resulting seeds were planted in a controlled environment. The new variety is named 'POULdrik'.

The new rose may be distinguished from its seed parent, MACrexy, by the following combination of characteristics:

1. The seed parent has over 40 petals per bloom, while 'POULdrik' has 14 to 18 petals;

2. The seed parent has light to medium pink flowers, while 'POULdrik' has coral pink flowers.

The new variety is similar phenotypically to the pollen parent, an unnamed seedling created by the same inventors, in that both varieties are floribundas with semi-double pink flowers.

The objective of the hybridization of this rose variety for garden use was to create a new and distinct variety with unique qualitites, such as:

1. Uniform and abundant coral pink flowers;

2. Vigorous, compact growth;

3. Cold hardiness and disease resistance.

This combination of qualities is not present in previously available commercial cultivars of this type and distinguish 'POULdrik' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULdrik' was selected by the inventors in the spring of 1988 as a single plant from the progeny of the aforementioned hybridization.

Asexual reproduction of 'POULdrik' by traditional budding was first done by L. Pernille and Mogens N. Olesen in August, 1989. This initial and other subsequent propagations conducted in controlled environments have demonstrated that the characteristics of 'POULdrik' are true to type and are transmitted from one generations to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULdrik'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULdrik', as observed in its outdoor growth in a field nursery in Jackson County, Oregon. Observations were conducted during October, 1998, on an eighteen month old plant. Color references are made using The Royal Horticultural Society (London, England) Colour Chart, 1995, except where common terms of color are used.

For a comparison, several physical characteristics of the rose variety 'POULander', a rose variety from the same inventors described and illustrated in U.S. Plant Pat. No. 6,265 and issued on Aug. 30, 1988 are compared to 'POULdrik' Chart 1.

CHART 1

| | 'POULdrik' | 'POULander' |
|---|---|---|
| Flower bud color, as sepals divide. | Red Group 44D. | Red Group 46A. |
| Color, upper petal surface, upon opening. | Red Group 41B to Red Group 40C. | Red Group 46B TO 46C. |
| Petalage under normal conditions. | 14–18 petals | Approx. 20 petals. |

Parents:

*Seed parent.*—MACrexy.

*Pollen parent.*—An unnamed seedling.

Classification:

*Botanical.*—*Rosa hybrida.*

*Commercial.*—Floribunda.

FLOWER AND FLOWER BUD

Blooming habit: Continuous.

Flower bud:

*Size.*—Upon opening, 35 mm in length from base of receptacle to end of bud.

*Bud form.*—Short, pointed ovoid.

*Bud color.*—As sepals unfold, Red Group 46D. Red Group 46B at ¼ opening.

*Sepals.*—Color: Upper side: Yellow-Green Group 144A. Lower side: Yellow-Green Group 144A. Shape: Sepals are cirrose at apex, with a flat base where they join with the receptacle. Size: Sepals are approximately 15 mm long by 10 mm wide. Extensions: Small foliaceous appendages on two to three sepals. Texture: Interior surface of sepals and sepal margins are moderately pubescent. Exterior surface of sepals lacks pubescence. Stipitate glands are present in very limited numbers on margins of sepals.

*Receptacle.*—Surface: Smooth. Shape: Funnel shaped. Size: Small, 8 mm (h)×6 mm (w). Color: Yellow-Green Group 144A.

*Peduncle.*—Surface: Smooth. Stipitate glands lacking. Length: 30–60 mm average length. Color: Yellow-Green Group 146A. Strength: Strong.

*Borne.*—Normally with 2–4 buds per flowering stem.

Flower bloom:

*Fragrance.*—None.

*Duration.*—As a cut flower 2 to 4 days. The blooms have a duration on the plant of approximately 6 to 7 days. Petals fall cleanly away from plant.

*Size.*—Average flower diameter is 60 mm when open.

*Form.*—Semi-double.

*Shape of flower when viewed from the side.*—Upon opening, upper part: Flat. Upon opening, lower part: Flat. Open flower, upper part: Flattened convex. Open flower, lower part: Flattened convex.

*Petalage.*—Semi-double. Average range 14–18 petals under normal conditions. With 1–3 petaloids.

Color:

*Upon opening, petals.*—Outermost petals: Upper Surface: Red Group 41B. Reverse Side: Red Group 50B. Innermost petals: Upper Surface: Red Group 40C. Reverse Side: Red Group 43C.

*Upon opening, basal petal spots.*—Outermost petals: Outer Side: Green-Yellow Group 1C. Inner Side: Green-Yellow Group 1A. Innermost petals: Outer Side: Green-Yellow Group 1A. Inner Side: Green Yellow Group 1A.

*After opening, petals.*—Outermost petals: Upper Surface: Red-Purple Group 70C and 70D. Reverse Side: Red-Purple Group 73A and 73B. Innermost petals: Upper Surface: Red-Purple Group 70D. Reverse Side: Red-Purple Group 73A and 73B.

*After opening, basal petal spots.*—Outermost petals: Outer Side: Yellow-Orange Group 14C. Inner Side: Yellow-Orange Group 15C. Innermost petals: Outer Side: Yellow-Orange Group 14C. Inner Side: Yellow-Orange Group 15C.

General tonality: On open flower Red-Purple Group 64D. No change in the general tonality at the end of the 4th day. Afterwards, general tonality is Red-Purple Group 66D.

Petals:

*Petal reflex.*—Slight.

*Petal edge.*—Slightly ruffled.

*Shape.*—Rounded, obovate.

*Petaloids.*—3–4 petaloids. Petaloids are small relative to petals. Petaloids are thin, and colored Red-Purple Group 64D on the outer side, Red-Purple Group 70C and 70D on the inner side.

*Texture.*—Smooth.

*Arrangement.*—Open, not imbricated.

Reproductive organs:

*Pollen.*—Color: Yellow-Group 13A. Quantity: Average.

*Anthers.*—Size: 12–16 mm. Color, mature: Yellow Group 12B. Quantity: 20–25. Pistils: 20–25.

*Filaments.*—Color: Yellow-Orange Group 17A.

*Stigmas.*—Stigmas are at the same position as the anthers. Color: Yellow Group 3B.

*Styles.*—Color: Yellow-Green Group 150B. Size: 8–10 mm.

*Stamens.*—Color: Yellow Group 12B. Size: 6–8 mm.

*Hips.*—None observed.

PLANT

Plant growth: Moderately bushy. After two seasons, the average height of a budded field grown plant on *R. multiflora* understock is 100 cm and the average width is 90 cm.

Stems:

*Color.*—Young wood: Yellow-Green Group 146C. Older wood: Yellow-Green Group 147B.

*Thorns.*—Incidence: 10 to 15 per 10 cm length of stem. Size: Average length: 10 mm–12 mm. Color: Yellow-Green Group 146D with the margins having intonations of Greyed-Red Group 180C. Shape: Concave.

*Surface.*—Young wood: Smooth. Older wood: Smooth.

Plant foliage: Normal number of leaflets on leaves halfway up a typical stem: 5 leaflets.

*Leaf size.*—Medium. 95 mm (l)×70 mm (w).

*Abundance.*—Average.

*Color.*—Upper Leaf Surface: Yellow-Green Group 147A. Lower Leaf Surface: Yellow-Green Group 147C. Juvenile Foliage: Upper Surface: Yellow-Green Group 147B, with intonations of Greyed-Purple Group 183B. Lower Surface: Yellow-Green Group 147B, with intonations of Greyed-Purple Group 183B. Anthocyanin intonation: Yes. Location: New leaves, stems, rachis, petioles, lower leaf surfaces, and peduncles. Color: Greyed-Purple Group 183B.

Plant leaves and leaflets:

*Stipules.*—Size: 15 mm (l)–3 mm (w). Color: Yellow-Green Group 146B. Stipitate glands present along margins and upper surfaces of stipules.

*Petioles.*—Length: 20 mm. Color: Yellow-Green Group 146B. Underneath: Typically smooth. Margins: With limited glands.

*Rachis.*—Color: Yellow-Green Group 146B. Underneath: Smooth with occasional small prickles. Margins: With moderate numbers of stipitate glands.

*Leaflet.*—Edge: Serrated. Shape: Broadly ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is moderately glossy. Lower side of leaflet is matte.

Disease resistance: Average resistance to black spot, and Botrytis under normal growing conditions in Jackson County, Oregon.

Cold hardiness: 'POULdrik' has been found to be resistant to damage from cold in USDA Zone 8 and USDA Zone 7.

We claim:

1. A new and distinct variety of rose plant of the floribunda class, substantially as herein illustrated and described as a distinct and novel rose variety due to its abundant, pink flowers, vigorous growth, disease resistance, and extended period of bloom.

* * * * *

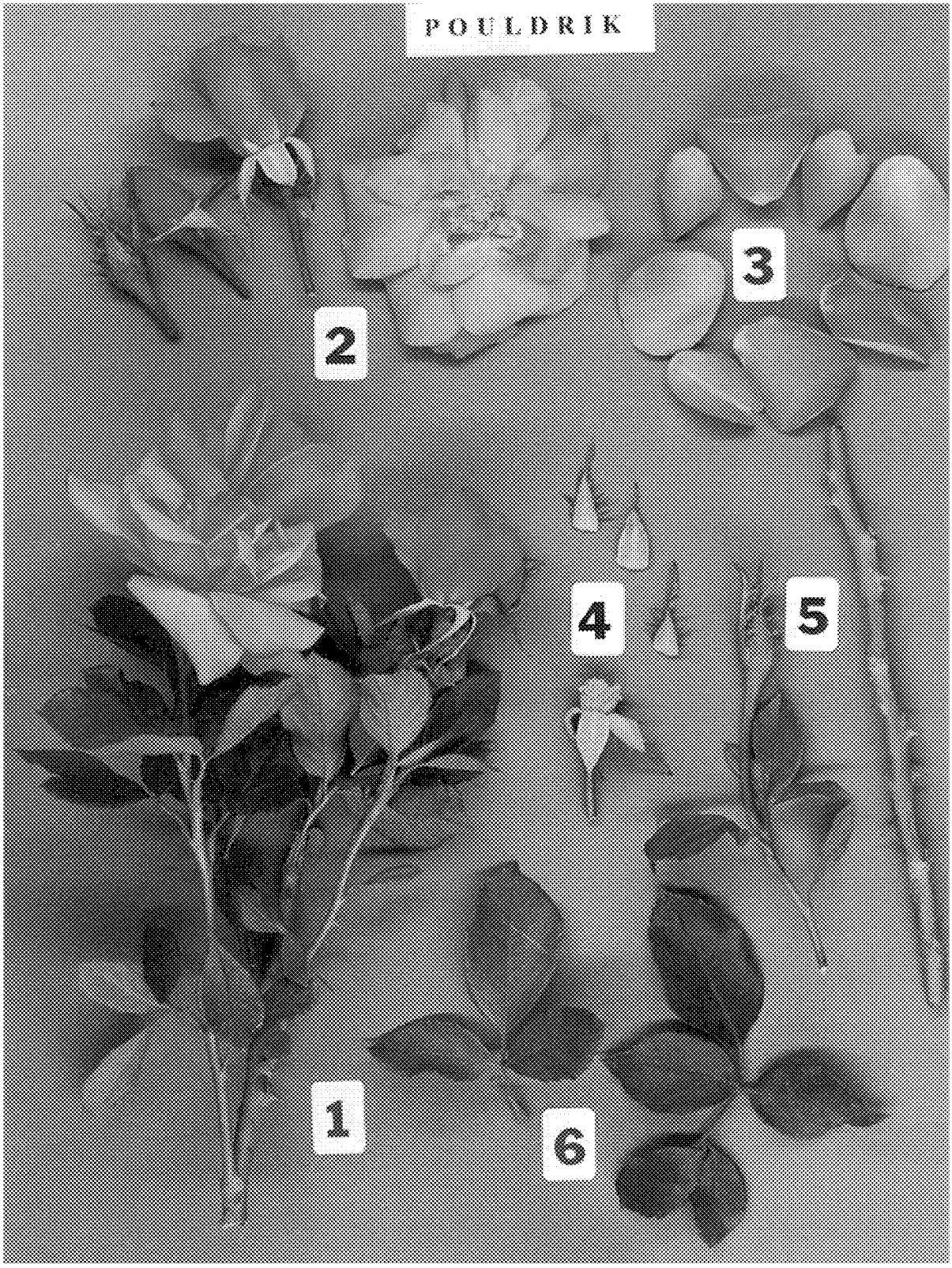
POULDRIK
1
2
3
4
5
6